United States Patent [19]

Dieterich

[11] 4,393,876
[45] Jul. 19, 1983

[54] SHOE ORTHOSIS OR SHOE ORTHOSIS PARTS

[76] Inventor: Alfred Dieterich, Westtorgraben 3, Nürnberg, Fed. Rep. of Germany

[21] Appl. No.: 264,110

[22] Filed: May 15, 1981

[30] Foreign Application Priority Data

May 22, 1980 [DE] Fed. Rep. of Germany ....... 3019561
Apr. 6, 1981 [DE] Fed. Rep. of Germany ....... 3113820

[51] Int. Cl.³ .............................................. A43B 7/24
[52] U.S. Cl. ................................................. 128/583
[58] Field of Search .............. 628/583, 584, 585, 581, 628/80 R

[56] References Cited

U.S. PATENT DOCUMENTS 1,012,017 12/1911 Salt ..................................... 128/583
1,340,700 5/1920 Dahl .................................... 128/583
3,470,879 10/1969 Meiller ............................... 128/583
3,550,597 12/1970 Coplans ............................. 128/585
3,731,323 5/1973 Glancy ............................... 128/583
3,929,139 12/1975 Salzman ............................. 128/583

Primary Examiner—John D. Yasko
Attorney, Agent, or Firm—Holman & Stern

[57] ABSTRACT

A shoe orthosis device for corrective treatment of foot deformities such as flat-foot, bent foot, splay-foot, hammer toes, hallux valgus, and others, comprising a sole member having a force transmitting mechanism and a foot pressure plate mounted thereon so that downward force at the heel during walking will be transmitted to the forefoot region to rotate and/or transversely move the forefoot, and great toe, and press the toes downwardly to correct the deformities.

19 Claims, 13 Drawing Figures

SHOE ORTHOSIS OR SHOE ORTHOSIS PARTS

BRIEF SUMMARY OF THE INVENTION

The invention concerns an orthopedic shoe appliance or shoe appliance component with a mechanism for corrective treatment of foot deformities, whereby the pressure force of the rear part of the foot on the appliance or appliance component is transmitted to the part of the foot which is being treated, in an intermittently acting force. An orthopedic sandal of this type was proposed in U.S. patent application Ser. No. 78,715 filed Sept. 25, 1979, now Patent No. 4,244,359, for corrective treatment of "hammer toe" and possibly also for correction of the X-position of the great toe. A similar orthopedic sandal of this type is the subject of the prior U.S. patent application Ser. No. 940,064, filed Sept. 8, 1978 now abandoned.

The underlying problem solved by the invention consists primarily of devising an orthopedic shoe appliance, or shoe appliance parts, such that an intermittent corrective treatment of such foot deformities is possible, whereby the position of the bones of the foot part of the foot is corrected with respect to the rear part of the foot (heel) by means of tensile, compressive, and/or torsional stresses. Further, the means for accomplishing these corrections, including correction of hallux valgus (a great toe partially stiffened in the basal joint in the X-position), which is mostly connected with a disorder of toes 2 through 5 in the form of so-called "claw-toes" and "hammer toes", should be made as simple as possible, so as to keep the manufacturing cost low and to ensure that the practical embodiment is as simple and durable, (sturdy and strong) as possible.

To solve this problem, the invention provides, first of all, means subjected to force, which turn the front part of the foot around the longitudinal axis of the foot and/or move it laterally around an axis running perpendicularly to the sole of the foot, whereby said means grip the medial side of the front part of the foot so as to lower (i.e., push down on) said front part of the foot "to lower it", thus working a rotation of said forefoot. The base piece of the shoe appliance may be a sandal or a shoe and the inventive mechanism component may be a mechanism which is installable in the shoe, which generally is a special shoe. The following foot deformities are correctively and intermittently treated by means of the invention, either with the foot in the resting position, where the foot is pressed against the floor or ground with an appropriate rhythm by the wearer, or, preferably, in the course of walking.

Collapsed or bent flatfoot, i.e., flatfoot and talipes valgus, can be successfully treated by relative turning or twisting (wringing) of the front part of the foot relative to the rear part (the heel). This deformity is acquired partly by heredity (i.e., hereditary predisposition) and partly as a result of defective tension due to connective tissue weakness. In "bent foot" (pes valgus abductus) the normally vertical axis of the heel has an X position relative to the vertical axis of the lower leg, i.e, the two legs form an X when the patient stands with feet together.

The so-called flatfoot is usually a combination of fallen arches, pes supinatus, and often also splayfoot (talipes valgus).

"Fallen arches" is understood to means reduced curvature of the so-called "longitudinal arch" of the foot, recognizable by a lowering of the inner (medial) side of the foot; "splayfoot" is understood to mean the reduced curvature of the so-called "transverse arch", easily recognized by the widening of the anterior part of the foot. "Pes supinatus" is the term applied to the condition where even at rest the inner edge of the foot is higher than the outer edge, so that the anterior inner (medial) edge of the foot bears less weight and the outer ("lateral") side bears more weight. If the "X-position" of the heel is subjected to correction by means of known bent-flatfoot (or collapsed flatfloot) devices, the load on the outer edge of the anterior part of the foot is further increased (and this is aggravated in the case of pes supinatus), so that the inner (medial) edge of the foot, i.e., of the anterior part of the foot, no longer even contacts the bottom support, or contacts it to a reduced degree. This situation is not changed by the Hohmamnn "detorsion" device, another known appliance, which has elevation of the anterior outer edge. In contrast, the invention provides, advantageously in the course of correcting bent-flatfoot, for the anterior part of the foot to be brought out of its harmful supinated position and to be suitably turned (twisted). This turning motion also increases the longitudinal arching, i.e., reduces the fallen arch deformity. This effect is achieved particularly well if the inner edge of the foot is supported with an arch support in the region immediately anterior to the heel. Additionally, it should be noted here that the medial lowering of the anterior region of the foot under the turning or twisting according to the invention the additional advantage of correcting splayfoot at the same time, i.e., the transverse arch of the anterior part of the foot is made more arching when, as described, the inner edge of the said anterior part is lowered; at the same time, the middle part of said anterior part is supported by inserting a so-called "splayfoot pad" on the sole.

Further, the invention may be used to treat pes adductus ("sickle foot"). This is a foot deformity in which the anterior part of the foot bends too far inward. The condition is usually also accompanied by pes supinatus (described above). Both of these deformities are the most frequently encountered elements of clubfoot, which is predominantly a congential defect. Until now, treatment of clubfoot by auxiliary means has been only by shoe inserts, shoe fitting, special "anti-varus" shoes, and various other orthopedic aids (orthoses), all of which exert a constant corrective (pressure) force on the foot. The disadvantage of these approaches is the ill effects of the pressure, i.e., discomfort, interference with circulation, psychic effects, and the acknowledged relatively poor therapeutic result.

The invention gives a much better result medically than prevriously known corrective treatments, in the treatment of bent flatfoot, sickle foot, and pes supinatus, chiefly due to the large number of individual intermittent actions as the patient walks. Also important is the fact that the invention is much better tolerated than the previously aids in common use. A further advantage is the fact that the inventive orthopedic shoe appliance components can be produced at low manufacturing and assembly cost. In particular, the costs involved are incomparably less than the costs of the alternatives, such as surgery and physiotherapy.

The invention also allows very simply achieved correction of X-position of the great toe (hallux valgus) along with deformations of toes 2 through 5 which may occur concurrently (in the form of so-called "claw toes" or "hammer toes").

The inention further concerns a series of mechanisms and means which impart the desired corrective movement to the respective foot parts as the patient walks. These means may be rods or (in a preferred embodiment) rollers on sliding surfaces as well as straps or cables.

Additional features of the invention will be seen from the following description and the associated drawings of exemplary embodiments of the invention.

DETAILED DESCRIPTION

The example of FIGS. 1 through 4 shows a dynamic bentflatfoot device. Here with each pressing of the heel, particularly with each walking step, the lateral part of the heel and the medial part of the anterior region of the foot are pressed downward. The direction in which the anterior part of the foot is rotated is opposite to that in which the heel is rotated (around the longitudinal foot axis) and the desired wringing effect is produced. The embodiment of these Figures is to be regarded as merely an example and is described in more detail below.

Figure 3:
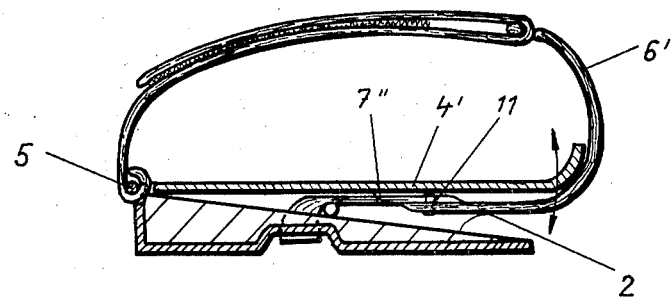
FIG. 3 is a cross-section taken along line III—III of FIG. 1.

The basic insole element 1 comprises, e.g., elastic cork approximately 1 cm thick. As shown in FIG. 3, the anterior foot part of the insole element is inclined by, e.g., 15° on its upper side 2 to promote the intended pronation (medial lowering) of the foot.

Herein the term "lateral" refers to the longitudinal side of the foot which is located on the outer side of the foot, and the term "medial" refers to the longitudinal side of the foot which is located on the inner side of the foot.

Figure 4:
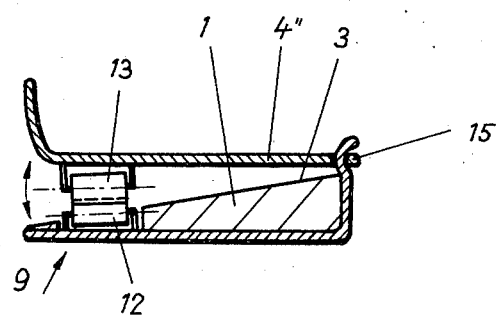
FIG. 4 is a cross-section taken along line IV—IV of FIG. 1.

FIG. 4 shows how in contrast to FIG. 3, the heel part of the insole element is inclined to promote supination (lateral lowering) of the heel, with the load surface 3 inclined outwardly (lateral lowering), also at, e.g., 15° to the horizontal. Above the insole element 1 and surfaces 2 and 3 there is the elastic stepping surface 4 of the insole, which may be comprised of, e.g., a plastic (such as that having the trade name "Ortolen"). Stepping surface 4 is swingably attached to the sole by means of hinge-like suspensions, e.g. a pin hinge 5 at the anterior lateral side of the stepping surface 6 for the ball of the foot, and a similar suspension (pin hinge) 15 on the medial side of the heel region. Instead of these hinges a single-piece material of suitably bendability and rigidity may be used. The insole element may be specially stabilized in the region of the elements 5, 15, 12, and 13 (see description infra), e.g. by plastic or a light metal. Strap 6 serves as a connection between the stepping surface and the anterior part of the foot, and can be adjusted continuously in length and locked, over the dorsum of the foot (with locking accomplished, e.g., by means of a chain catch or burr fastener). The strap may either be attached to both edges of the sole 4' (this double attachment is not shown) or, according to a preferred embodiment (shown particularly in FIG. 3), it is attached to the lateral side of the sole, and the medial segment of the strap 6' runs over a sliding-surface on the edge of load surface 4' and merges into tension strap 7", instead of being attached to the medial edge of the sole. This provides the advantage of a functionally intensive contact of the forefoot with the corresponding stepping surface, resulting in stronger corrective action on pes supinatus and splayfoot. A strap or cord 7 is adjustably attached to the lateral side of heel 8 as at 7' and runs through the posterior edge of the heel and through a pulley mechanism 9 (discussed in more detail below) forward to a roller or sliding-surface 10 which may be located, for example, centrally under the ball of the forefoot or somewhat to the side. There the strap or cord 7 is bent upward as shown at 7" in FIG. 2. At this point strap 7 can be attached (not shown) to the bottom of part 4' of stepping surface 4 which is tiltable around hinge 5. In the preferred embodiment shown, this part 7" of the strap is joined at 11 to medial strap 6' (see FIG. 3). The tension in strap or cord 7 is made adjustable at its attachment at 7' and also via forefoot strap 6'.

Figure 1:
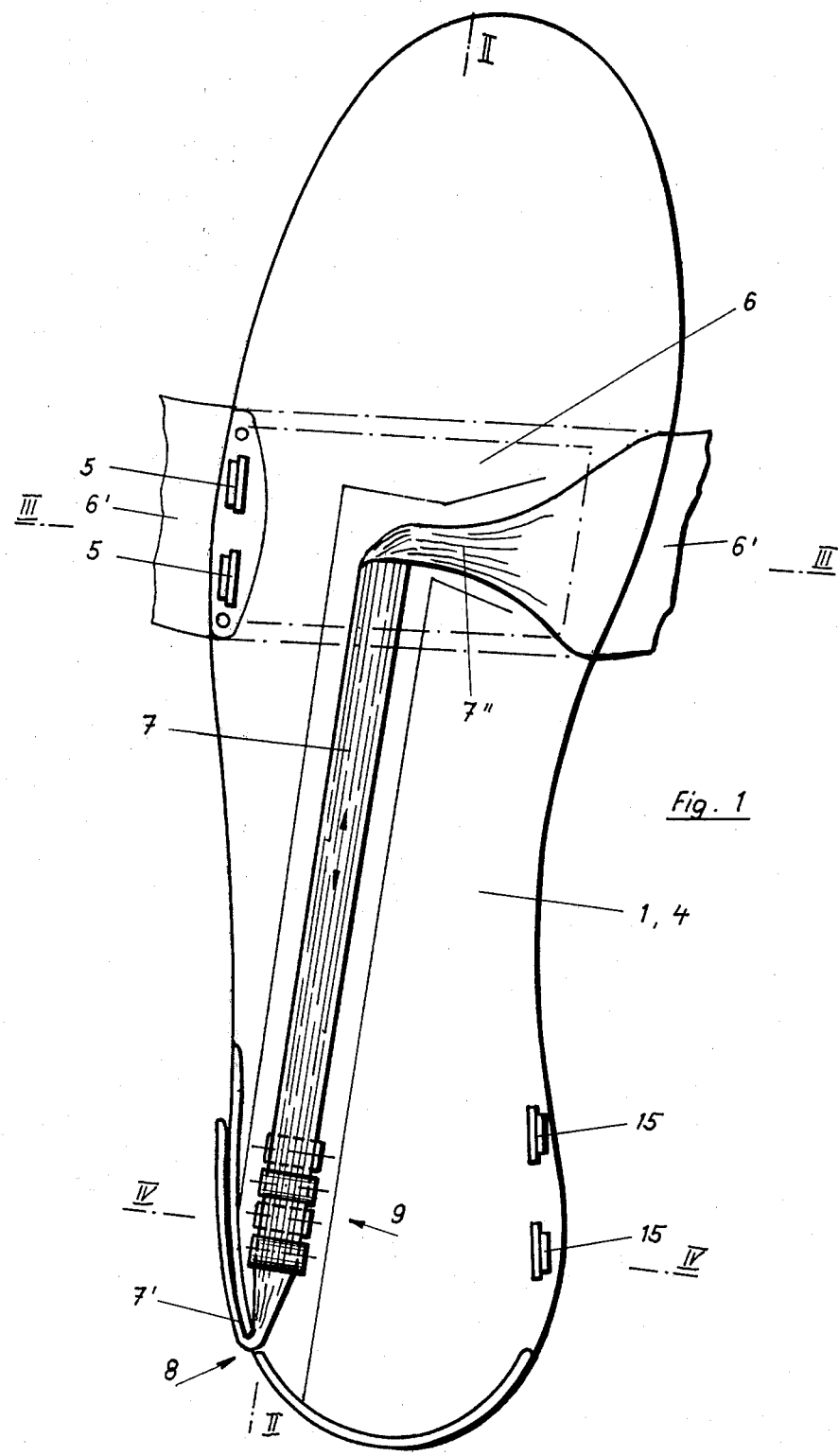
FIG. 1 shows a top plan view of a first example embodiment of the invention for treating a bent flatfoot having supination of the anterior part of the foot.
Figure 2:
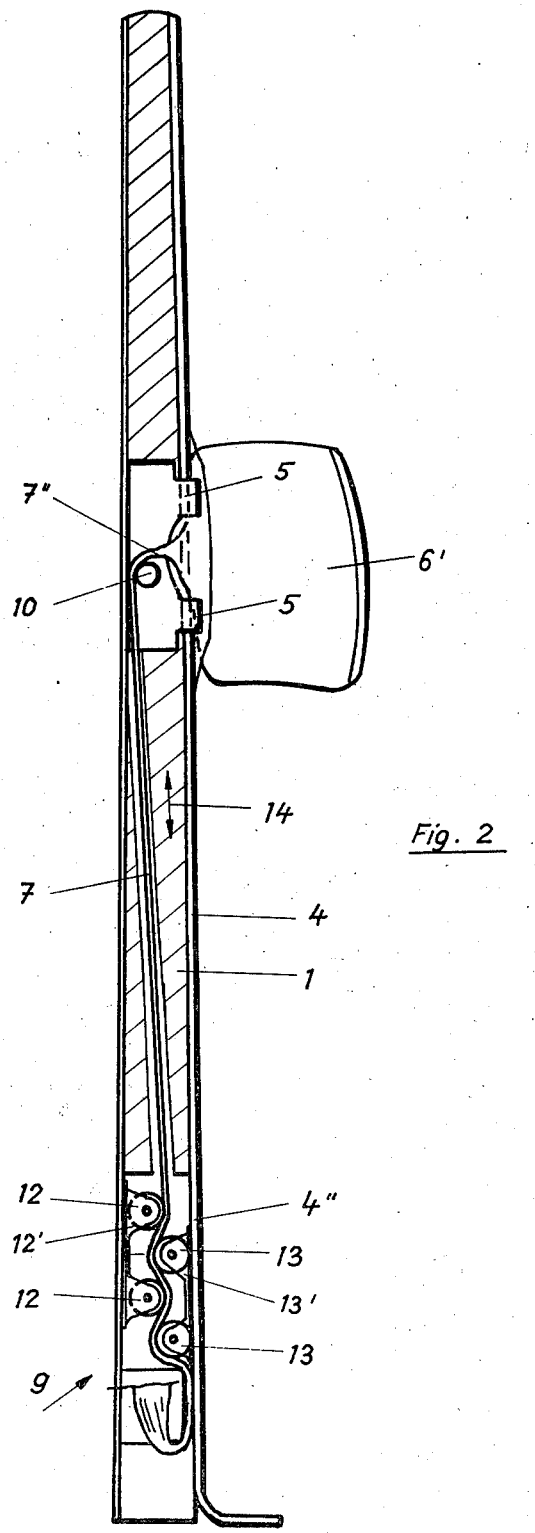
FIG. 2 is a cross-section taken along line II—II of FIG. 1.

The "pulley" mechanism referred to supra comprises (in this example) two rollers or sliding surfaces 12 rotatably mounted on brackets 12' in the heel part of insole element 1 and two rollers or sliding surfaces 13 rotatably mounted on brackets 13' on the underside of movable stepping surface 4, 4", whereby strap or cord 7 passes between rollers 12 and 13. As shown in FIG. 2, the rollers 12 and 13 are mounted in longitudinal staggered relationship with respect to each other with one of rollers 13 positioned between rollers 12 and one of rollers 12 positioned between roller 13 so that when surface 4" moves down (or up) by a distance x the strap or cord 7 moves a distance 4x in the direction of arrow 14, toward (or away from) the heel. The pulley-system principle illustrated may also be applied (with more or fewer rollers) for different intermittent corrective actions on foot deformities such as those described herein, as may be partially seen from the drawings. In the flatfoot-correction device according to FIGS. 1 to 4 the housing of this pulley mechanism in the lateral posterior heel region in particular is advantageous, since it is desired to have a supination tilting movement of the heel at the moment of loading of the heel for correction of bent foot, or talipes valgus. In this case the partially elastic, flexible heel stepping surface 4" should be swingably mounted in hinge fashion on its medial edge 15 and the part of the heel piece lying under it should be hollowed out in the shape of a wedge (FIG. 4). The insole should be worn in special support shoes or sandals with elastically bendable soles which give the forefoot the necessary elevation for the wringing motion and enable the middle and posterior parts of the foot to be properly held in place in the shoe. The heel mechanism (4", 12, and 13) goes into action as soon as a load is placed on the insole in the heel region. The rollers 13 attached to the underside of the insole move downward directly posterior to rollers 12 longitudinally fixedly attached in the heel, and thereby put tension on tension cord 7. Thereby, in turn, the medial forefoot region, including medial anterior part 4' of the insole, is pulled downward and the forefoot is pronated. The condition for the desired pronating rotational motion is a sufficiently light binding via the abovementioned middlefoot (metatarsal) strap 6' of the forefoot to the anterior part of the insole. A simultaneously provided sufficiently stable holding in place of the posterior part of the foot in the region of the steeply outwardly inclined heel stepping surface 4" results in the desired "wringing" action on the foot during the course of operation of the device, particularly when the stepping surface of the insole is appropriately shaped; and this "wringing" action is maintained as long as there is a load on the posterior part of the foot. When the load is removed i.e. at the end of the pushoff phase of walking, the foot is released from this "wringing" motion. The "wringing" of the foot by this insole not only corrects "bent foot" (talipes valgus) and pes supinatus but also increases the curvature of the longitudinal and transverse arches of the foot, i.e. has a corrective effect on fallen arch and splayfoot deformities. Arrows appear in the Figures to indicate the respective directions of motion during operation of the device.

As mentioned above, the entire arrangement may be inserted as an insole (which may be loose) into specially designed shoes having the proper inner clearance. It is also possible to construct the assembly in the form of an integral shoe orthosis, as a shoe or sandal.

The tensioning cord or strap 7 may also be tensioned by means of an increase in the circumference (perimeter) of a chamber which may be, e.g. lens-shaped, with deformable walls (e.g., a rubber or plastic bladder) and containing an incompressible liquid, so that the overall volume of the bladder is not substantially changed upon compression. The tensioning cord passes around the round circumference of the bladder and is slidably held in place by holding means. When the load is placed on the heel the chamber is compressed in approximately the vertical direction, whereby its walls can only expand in the horizontal radial direction, thus increasing the horizontal dimensions and tensioning the tensioning cord which is being held there (this arrangement is not shown in the Figures).

Instead of a tilting supination motion of the heel a similar effect can be brought about by a simple lowering of the heel using an appropriate simple mechanism, whereby when a load is applied the heel stepping surface of the insole is also lowered in the direction of the heel piece of the insole, as was the case in the above description of the first variant (this suggested mechanism is not illustrated).

Figure 5:
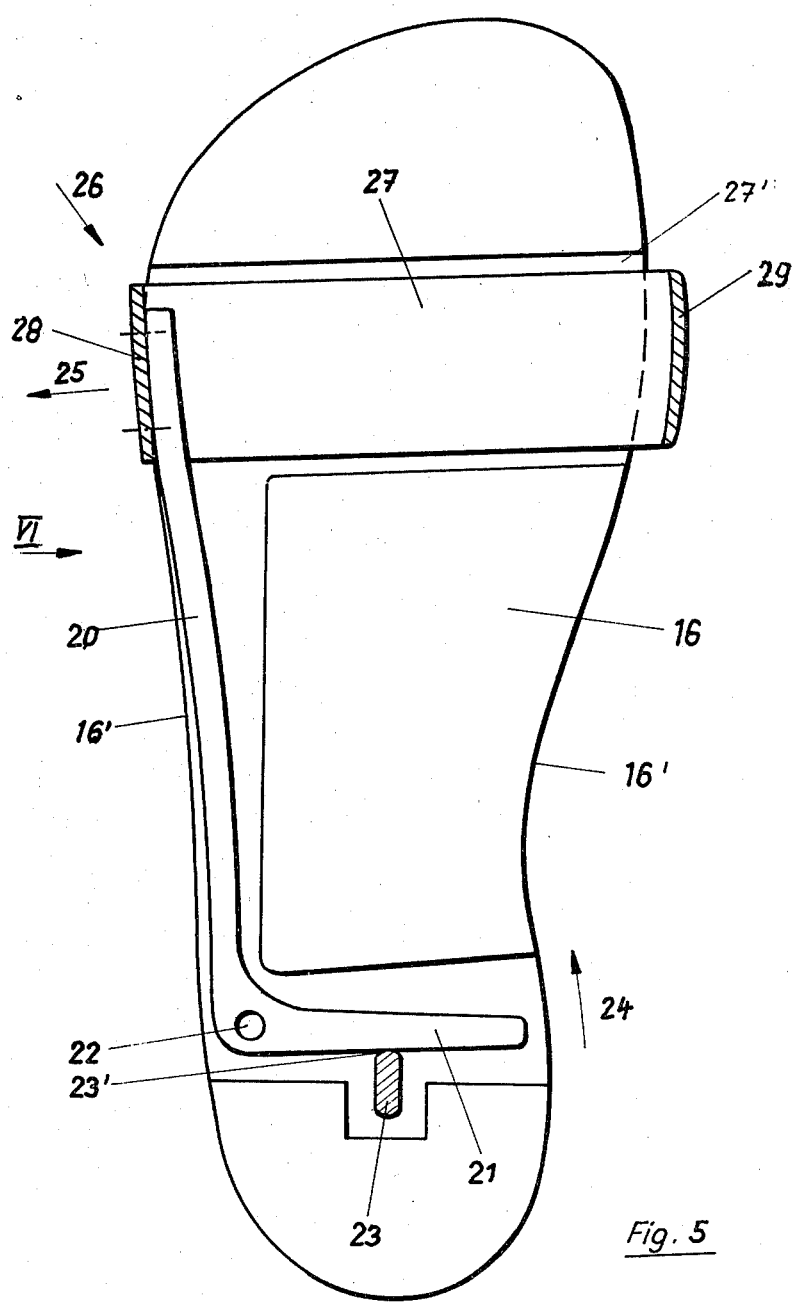
FIG. 5 is a top plan view of a second embodiment of the invention for treating sickle foot with possible additional pes supinatus.
Figure 6:
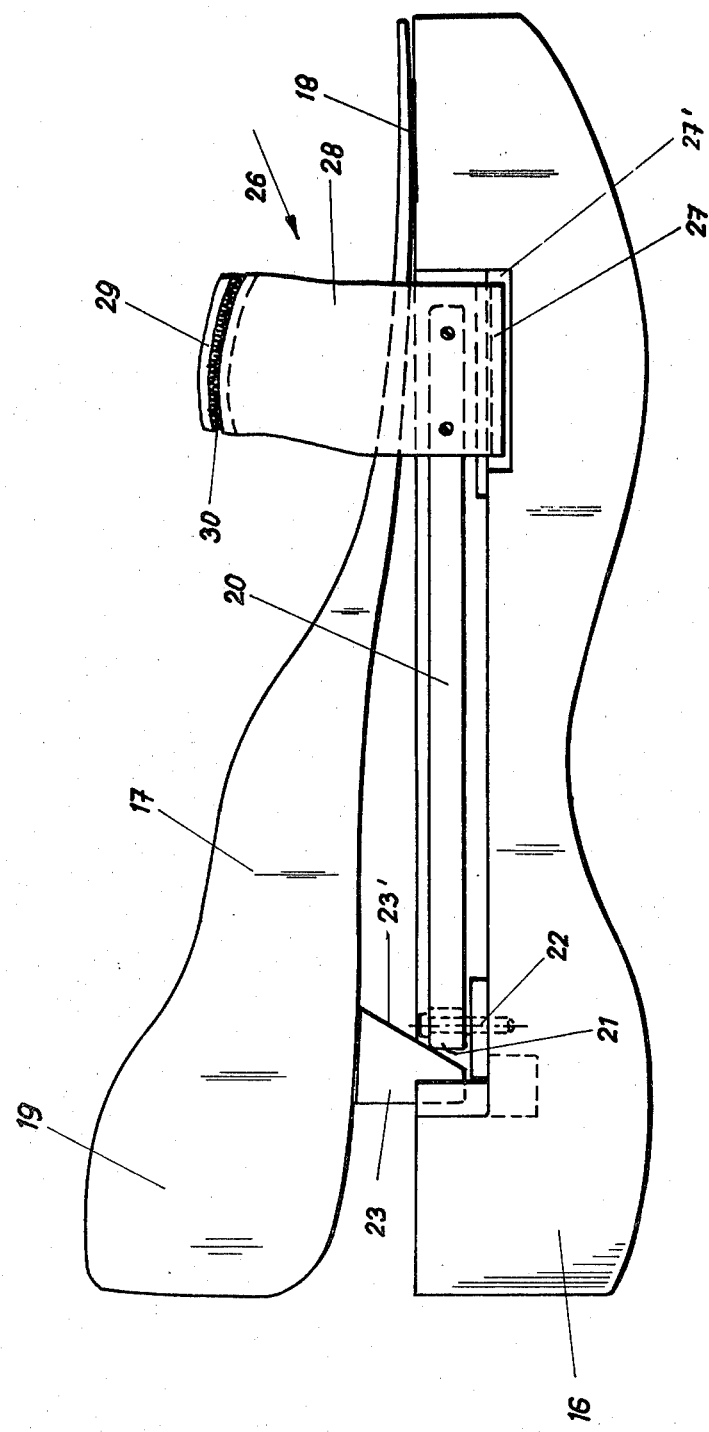
FIG. 6 is a left side elevational view of the embodiment of FIG. 5.

FIGS. 5 and 6 show an embodiment of the invention in the form of a sandal for treating "sickle foot" (pes adductus) in possible combination with pes supinatus. The sole 16 of the sandal supports a shell insole 17 for accepting the foot. (The insole 17 is not shown in FIG. 5 and certain parts are shown in sectrom to better illustrate the lever mechanism which will be discussed infra.) The shell insole 17 is fixed to sole 16 in the transverse direction, only in the region of the forefoot 18, and in its remaining extent it can be easily lifted. The lifting may be up to 3 cm at the heel part 19. A lever with the two arms 20 and 21 is pivotally mounted in cut out portions 20'-21' by pivot pin 22 which is vertically attached to the sole 16. To accomplish the pivoting movement lever arm 21, whch is preferably the shorter arm, is situated in the region of travel of a projection 23 on the underside of the heel part 19 of the shell insole. When this heel part moves downwardly, lever arm 21 is engaged by the front inclined edge 23' of projection 23 and moved in the direction, so as to force lever arm 20 (which is preferably the longer arm) in the direction of arrow 25. The force acting in the direction of arrow 25 not only corrects pes adductus ("sickle foot") but also the accompanying pes supinatus, in that the forefoot region is rotated such that the medial edge is lowered. This is accomplished with the aid of a double strap or loop or thong 26, the underneath part 27 of which runs through a hollow pathway 27' in the sole 16 beneath a stabile plate, and the two upper ends 28 and 29 of which (only partly shown in FIG. 5) are joined and supported above the foot with the aid of fastener 30, which may be the "Velcro" type. Thereby the foot is surrounded approximately in the region of the anterior half of the first metatarsal bone and including the fist phalanx of the great toe. The anterior end of lever arm 20 engages the side of the lower loop part 27, so that its sideways (lateral) motion in the direction of arrow 25 not only produces correction of "sickle foot" but also the rotational pronation motion of the forefoot discussed above, since the medial opening of the hollow pathway 27' is lower in the sole than the lateral opening due to pathway 27' being inclined transversely to the longitudinal axis, to provide a more favorable tensioning direction. (This inclination of the hollow path in the sole is not shown in the Figures.) This is advisable if one seeks to correct accompanying pes supinatus along with the pes adductus. At the same time the surface of sole 16 should be configured to provide a free space between the medial edge of the forefoot and said surface part of the sandal sole, to enable the abovementioned lowering of the medial edge during the operating phase of the device. When foot pressure is released from heel part 19 of the shell insole 17, the foot returns to its initial position, due to the fact of its deformity. In the posterior region the foot is held against the edges of the shell insole by a separate strap (not shown). As shown in FIG. 5, it is advantageous for the short lever arm 21 to be approximately transverse to the sandal longitudinal axis when it is in its rest position (not swung by projection 23). The lever ratio of the short arm 21 to the long arm 20 may be about 1:5, so that the movement at the anterior end of long arm 20 caused by heel part 19 via projection 23 is five times that of arm 21 at its contact point with surface 23'.

The basic concept of this part of the invention, namely production of a correcting action on pes supinatus as well as "sickle foot" (pes adductus), can also be accomplished in other ways, e.g., the heel part can actuate a toggle lever or a shear grid arrangement (not shown), via a part similar to projection, whereby (analogously to FIG. 5) the force is transmitted in the form of a lateral tension in the direction of arrow 25, to loop 26.

Also, a lever arrangement may be devised whereby a sufficiently wide, padded pressure plate is pressed against the medial dorsal side of the forefoot, thereby moving the forefoot in the direction of the corrective position.

The tensile force may also be exerted with the aid of a cord or cable which pulls loop 26 in the direction of arrow 25, over a guide roller. The tensile force may come from a short shaft having a tooth which engages a high-pitch thread, whereby when the heel part 19 is pressed the shaft is pressed downward and receives a rotational motion due to the coupling to the high-pitch thread. The cord, which is wound around the shaft, is thereby correspondingly tensed.

Instead of the underneath part 27 of the loop in the embodiment of FIGS. 5 and 6, a slide member may be provided there which is slidably housed in an appropriate hollowed out portion in the forefoot region of the sole. The slide member may then be slid laterally by the longer lever arm 20. A possible configuration for such a slide member is seen in the embodiment of FIGS. 7 to 9 which will be described below.

The embodiment of FIGS. 7 to 9 involves a dynamic sicklefoot or clubfoot corrective sandal, constructed as follows: The stabile sole, made of plastic or wood, for example, allows the forefoot region (FIG. 9) to assume a pronation position of the forefoot stepping surface 33 up to an angle beta (e.g., about 15°) which is variable via a wedge-shaped support. The sole 31 in this forefoot area has a wide groove 34 which receives the part of the slide member 33 which is shown horizontal in FIG. 9 as slidably mounted on slide or roller supports 34'. Further, the cord or strap 35 may run in this groove 34, being attached to the slide member at 36 and running transversely and downwardly from there. The slide member further comprises an extension 37 which extends approximately vertically upward at the level of the edge of the forefoot, from one of the ends of said slide member (in the embodiment illustrated this end is the lateral end, but it can be the medial end). The forefoot strap 38 is attached at one end to the medial edge of the sliding member and on the other end to the lateral edge (here at extension 37) and is adjustable, e.g. by means of a burr catch fastener. The tension in this semicircularly acting loop is thereby continuously adjustable. Accordingly, there is no hazard of excessive circular constriction.

The strap or cord 35 runs from point 36 approximately parallel to and beneath slide member 33 and over roller 39 which is rotatably mounted on a substantially vertical axis rearwardly to the actuator at the heel. In this case motion of the strap or cord produces a pure abduction (lateral) movement of the forefoot, aimed at correcting "sickle foot" (pes adductus). It is also possible to run the strap or cord 35 around a roller 40, which is rotatably mounted on a substantially horizontal axis and may alternatively be located at other positions 40' and 40'' on the sole. When it is in position 40'', tension on the strap or cord 35 basically results only in downward swinging of slide member 33, together with the cover or guide which surrounds it and is pivoted at point 41, around point 41 in the direction of angle beta. In this case the function of the sandal amounts to a basically pure pronation movement of the forefoot (medial lowering of the forefoot), aimed at correcting pes supinatus. If the roller is in position 40 or 40', a tension on strap 35 from the actuation of the heel mechanism produces a mixture of pronation and abduction of the forefoot (clubfoot correction with different strengths of the component forces).

Figure 7:
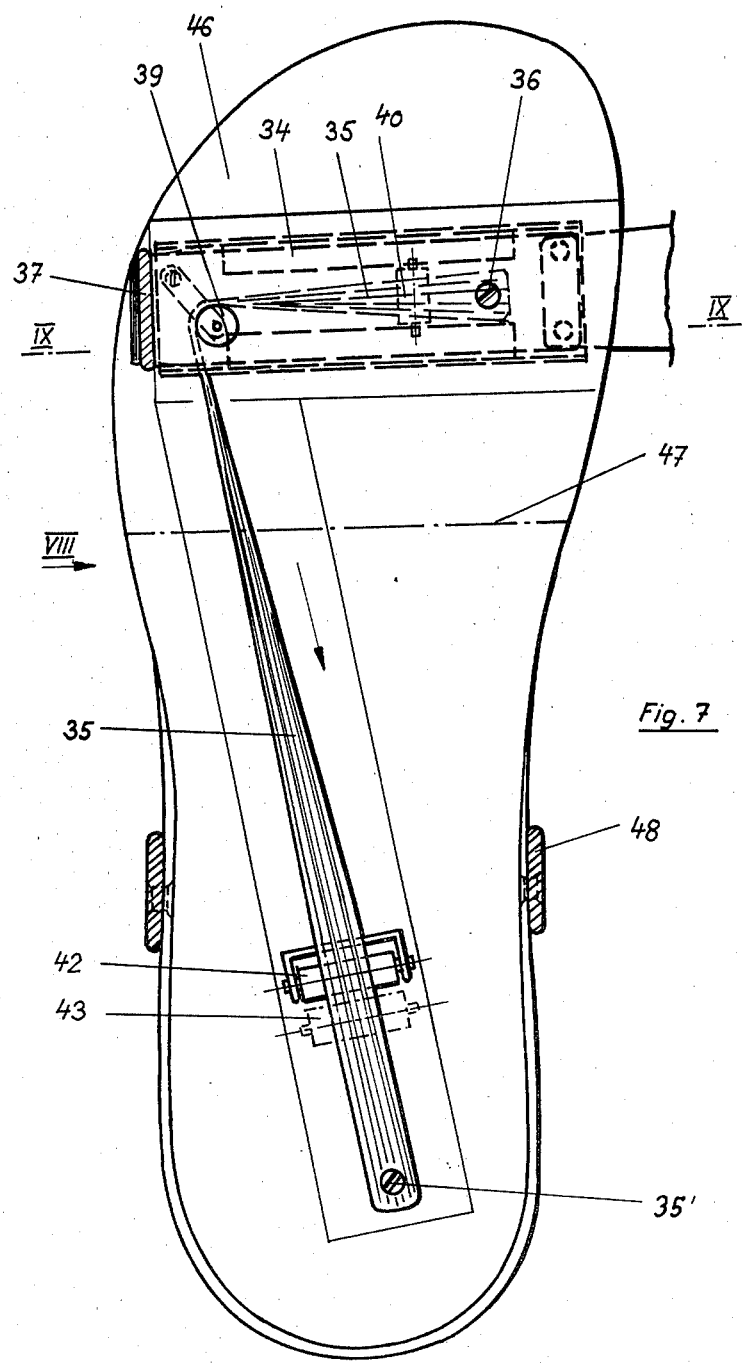
FIG. 7 is a top plan view of a third embodiment of the invention for treating sickle foot and/or pes supinatus.
Figure 8:
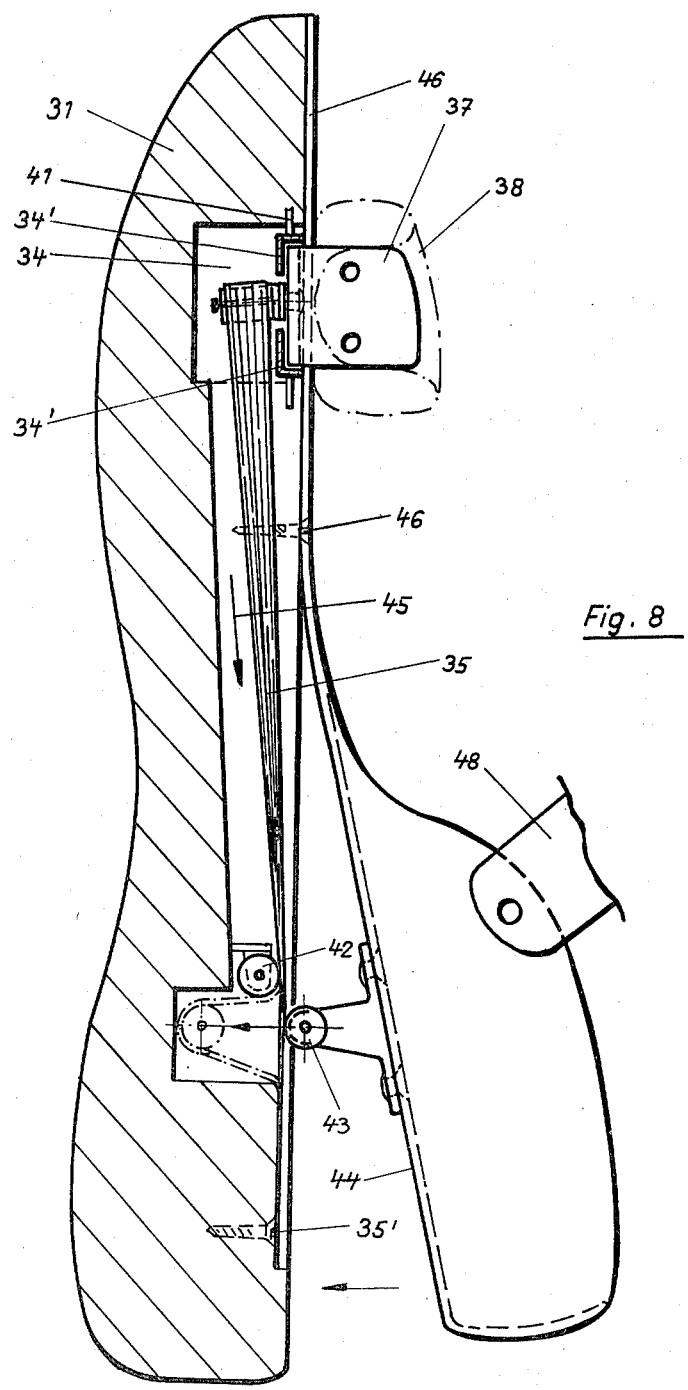
FIG. 8 is a partly sectional view of the embodiment of FIG. 7 as viewed from the left.
Figure 9:
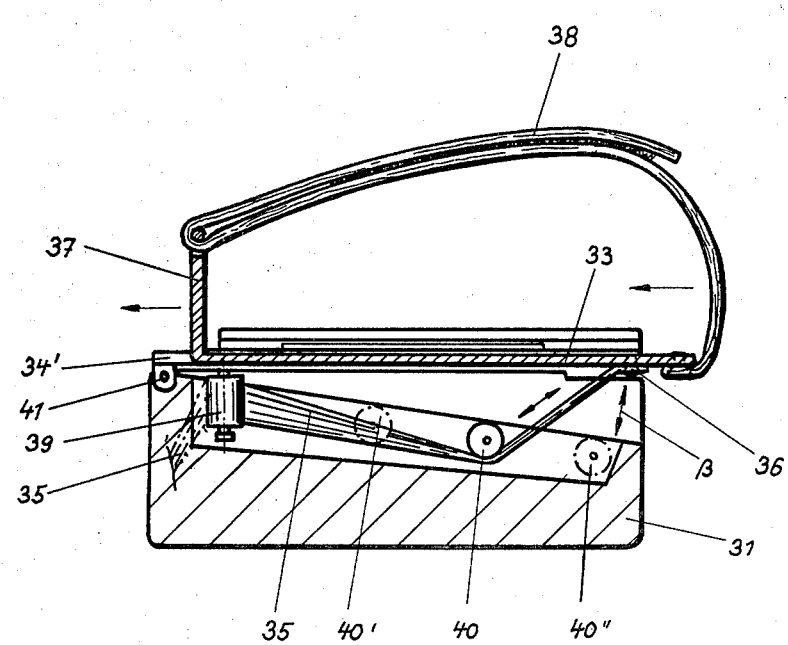
FIG. 9 is a cross-sectional view taken along line IX—IX in FIG. 7.

The path of the strap or cord 35 from the sliding member to the heel actuator is seen best from FIGS. 7 and 8. It runs in a longitudinal slot in the sole to the heel region, where it is attached to the sole at 35'. This attachment may be adjustable to allow variable pre-tensioning of the strap. This feature is also of practical value for band attachments in the other embodiments. In fact, it may be said generally of the embodiments that devices and means depicted in any of them may be advantageously applied to any of the others.

The inventive heel mechanisms here comprises two rollers (or suitable sliding-surfaces) rotatably mounted on parallel axes, with the anterior roller 42 mounted on the sole and the posterior roller 43 mounted on a bracket on the moving stepping surface 44. The strap or cord 35 runs over and between the rollers in such a way that the pulley, (grid) principle described above is utilized, whereby the downward motion of the stepping surface 44 is converted into a lateral motion of the cord in the direction of arrow 45, in the amount of twice the distance of the engaged downward motion of 44.

The stepping or load surface 44 may comprise a shell-shaped insole, made of, e.g., a molded resin, which is rigidly fastened to the sole 31 at 46, and which swings around a horizontal axis transverse to the longitudinal direction of the foot when the heel of the foot is set down. This axis is shown as the dot-dashed line 47 in FIG. 7. The fixed anterior part 46' of the stepping surface 44 covers over groove 34 to form a hollow passageway. The outer edges of the shell-shaped stepping surface 44 are rigid and strong, extending back to the posterior region of the foot, and the inner side is well padded. The posterior part of the foot (hindfoot) is held on the stepping surface by means of a broad strap 48 of a type commonly used on sandals.

It is noted that by means of the abovementioned individually adjustable tension of the forefoot strap 38, with each tensional movement of strap or cord 35 the forefoot is moved in an abduction and/or pronation movement. This corrective movement can be amplified by an appropriate pre-tensioning of the forefoot strap 38 or in the case of a sensitive foot it can be relaxed by relaxing the pre-tensioning.

As already discussed, the sliding member 33 may also be moved by a lever, e.g., by the lever arm 20 in the example of FIGS. 5 and 6.

Figure 10:
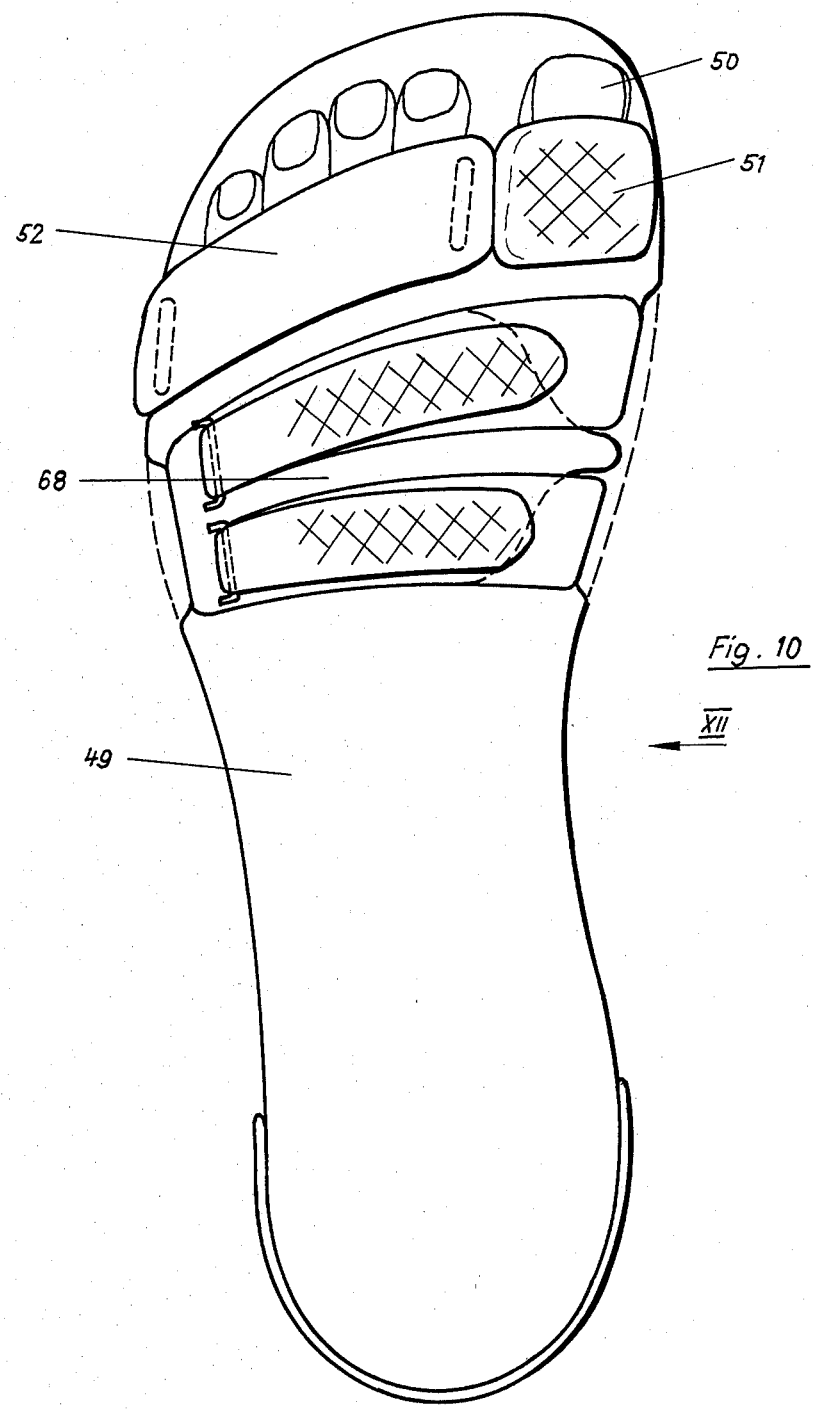
FIG. 10 is a top plan view of a fourth embodiment for treating hallux valgus and "hammer toes"
Figure 11:
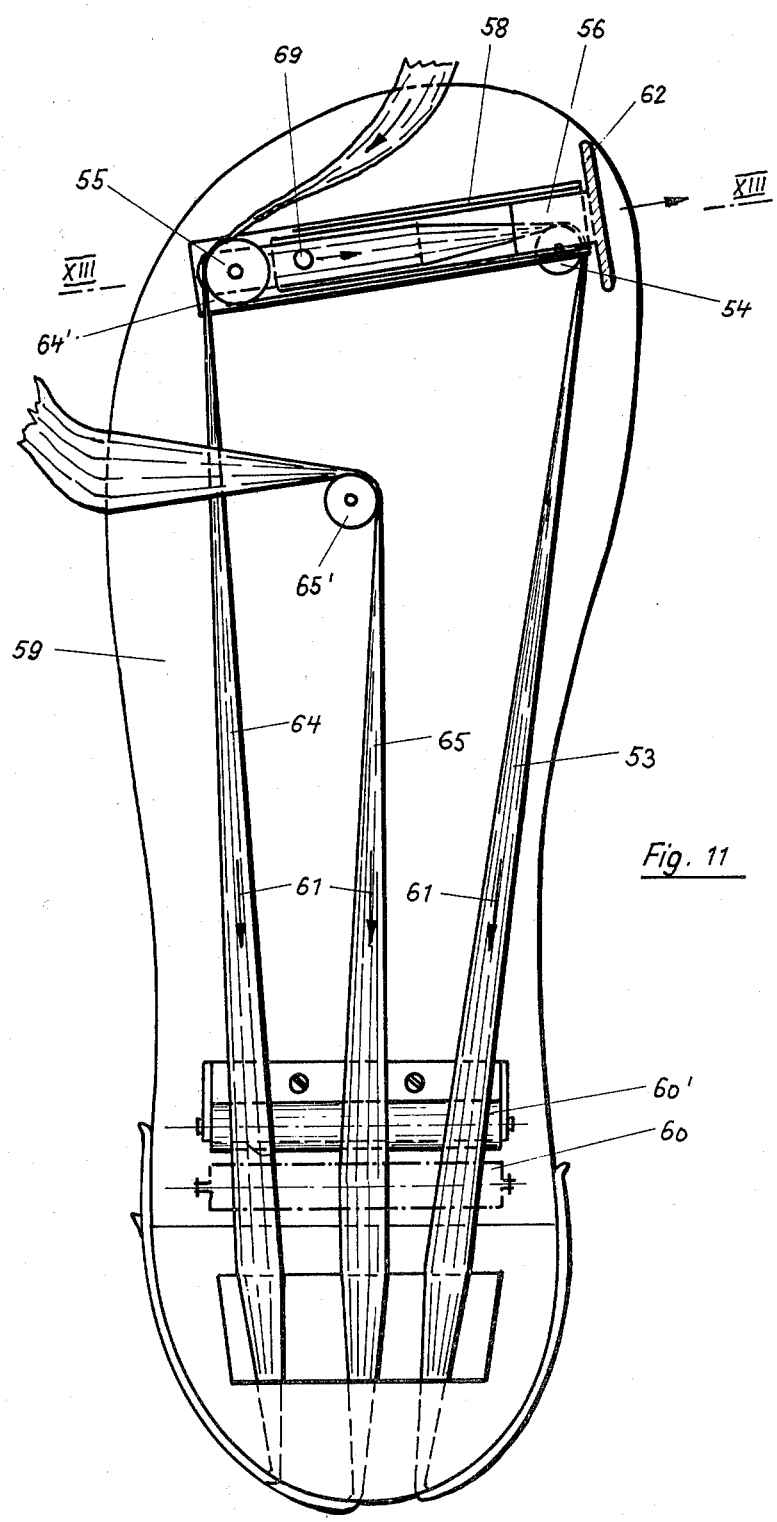
FIG. 11 is a top plan view of the embodiment of FIG. 10, but with the foot and the parts covering the toes removed.
Figure 12:
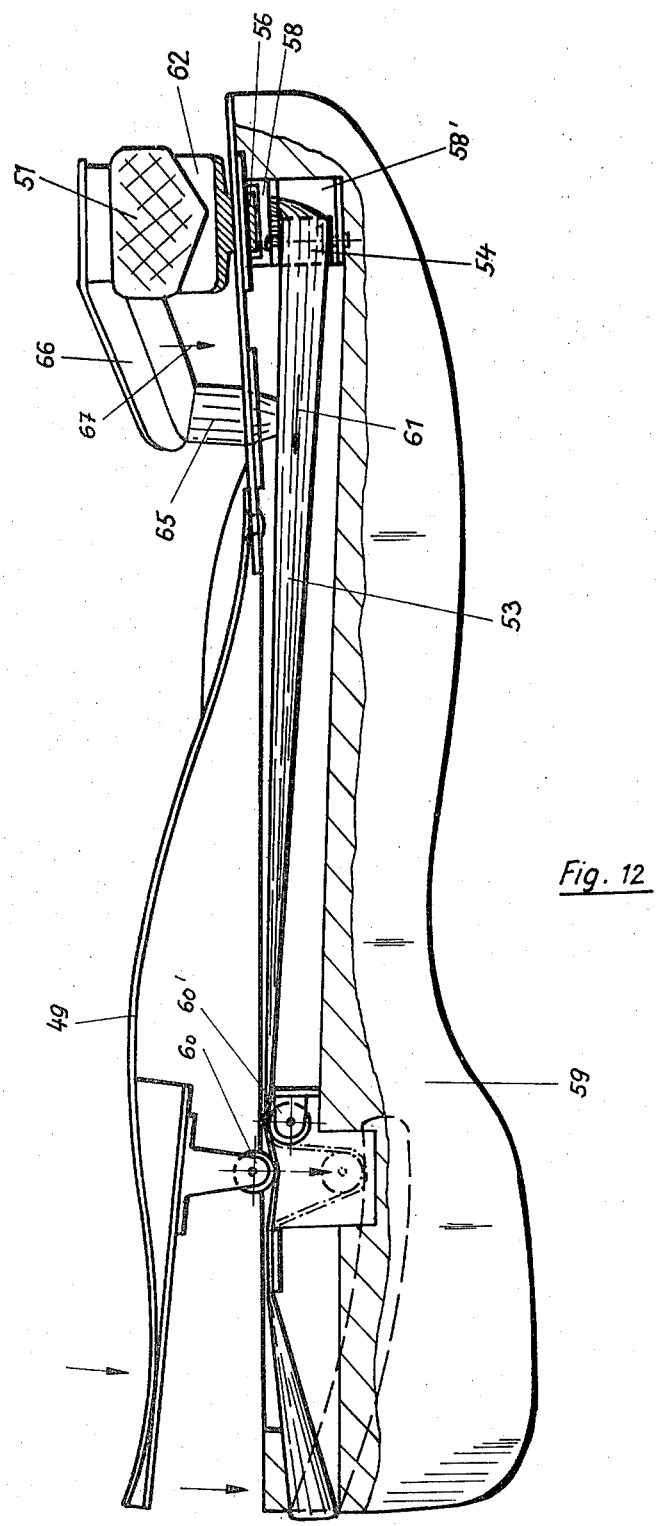
FIG. 12 is a partly sectional, side elevational view of the embodiment of FIG. 10 as viewed from the right.

The embodiment of FIGS. 10 to 13 shows the configuration of a sliding member which is basically similar to member 33 of the preceding embodiment and is used in correcting X-position of the great toe (hallux valgus). FIG. 10 is a schematic plan view, showing stepping surface 49, a loop 51 surrounding the great toe 50, and a pressure plate 52 for correcting the "hammer toe" position of the other toes.

Figure 13:
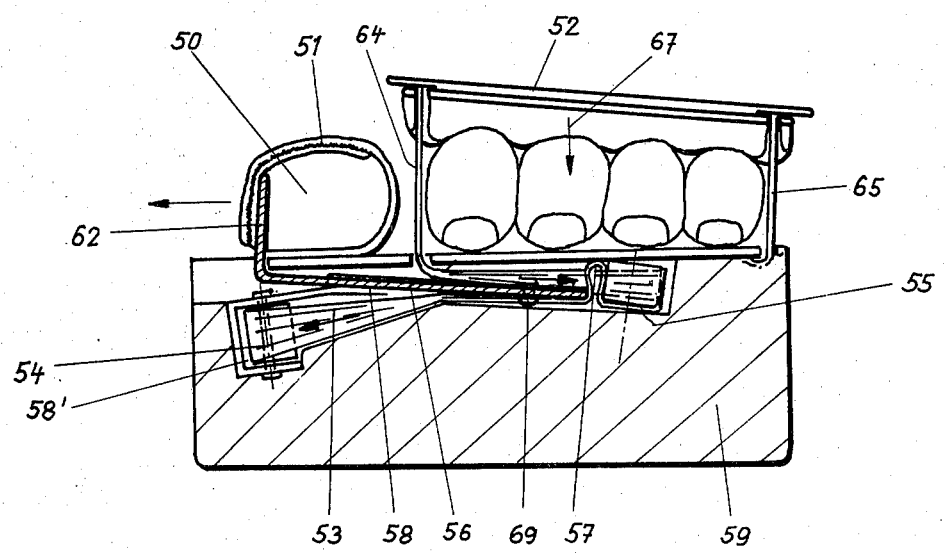
FIG. 13 is a cross-sectional view taken along line XIII—XIII of FIG. 11.

A strap or cord 53 is provided for correcting the X-position of the great toe. This strap or cord runs over a roller 54 rotatably mounted on an axis slightly angled to vertical (as shown in FIG. 13), or sliding surface, extends mainly transversely, but at a small angle, is attached to the underside of sliding member 56 at 69, and then continuing mainly transversely is attached to sole 59 nearby at 55. The strap 53 thus runs under sliding member 56 (FIG. 13) and forms a slack loop between its two fastening points 69 and 55. This loop is under tension only in the terminal or initial, position of sliding member 56, i.e., the extremety of its movement in the medial direction. The attachment of the end of the strap to the sole 59 prevents the sliding member from being pulled too far medially when the strap is pulled.

Sliding member 56 slides in a U-shaped guide channel 58 in sole 59 which has a larger opening 58' in its bottom portion for the strap 53 to pass through. Roller 54, mentioned above, is disposed in the medial region in the larger opening 58' of guide channel 58.

Downward movement of the heel support surface 49 causes the roller or sliding-surface 60 attached to the bottom of member 49 to also move downward. In combination with roller 60' mounted on sole 59 this produces a pull on strap 53, which passes between the rollers, in the direction of arrow 61, and thereby a medially directed sliding of sliding member 56. A holding loop 51 is provided on an upwardly directed extension 62 of sliding member 56. This loop has an adjustable length (e.g., via a burr fastener), and surrounds the great toe 50. With this arrangement the great toe is forced in the medial direction. Extension 62 acts to prevent the great toe from being excessively constricted by loop 51. The device described provides a substantial advantage due to its simple construction, and optimally furnishes a medially-directed loop tension without costly, annoying, or inconvenient structures on the medial edge of the shoe.

In conjunction with this hallux valgus corrective device, two straps 64 and 65 can be added which are also movable in the direction of arrows 61 when the mechanism 60 and 60' is actuated, to act on a "hammer toe" pressure plate 52 and move it downward in the direction of arrow 67 when the pull of straps 64 and 65 in the direction of arrows 61 occurs, whereby plate 52 presses on toes 2 through 5, and said toes are straightened in their joints which are excessively bent. This last-described device is indeed simple, since all the toes 2 through 5 are movable to correct "claw toe" or "hammer toe" with the use of only two straps. Strap 65 passes around roller 65' and strap 64 passes around roller 64', the rollers being positioned to direct the desired force on plate 66.

Straps 53, 64, and 65 are individually adjustable and attachable for each particular situation and to produce the desired pre-tensioning. This rest-stage tension adds to the dynamic operating tensioning of the entire device when the heel region of stepping surface 49 is moved downward. It is essential, particularly for the actuation of pressure plate 52, for straps 64 and 65 to each be independently adjusted to the appropriate effective length and to be attachable in the respective set-position, since from case to case different corrective actions on the inner and outer, i.e. medial and lateral, toes will be required, requiring correspondingly different corrective straightening of the lateral and medial toes 2 through 5. A sponge rubber like pad 65' may be provided on the underside of plate 52 which contacts the toes.

For correction of splayfoot (talipes valgus), a splayfoot band 68 is provided for the sandal of FIGS. 10 to 13, which band can be fastened adjustably by the use of burr-hock-fastener material, on the dorsum of the foot, in the desired holding position. In this way one may, on the one hand, deal with the pressure consequences of a possible hallux valgus exostosis, and on the other hand produce the support which is needed when correction in the form of medial movement of the hallux valgus is being carried out. Alternatively, this band 68 can serve to hold the forefoot in place against the sole. The two plantar strap ends of the band may each be joined to a respective strap analogous to straps 53, 64, and 65, and these straps from band 68 may be passed to rollers (or sliding surfaces) 60 and 60', thus enabling intermittent treatment of splayfoot (talipes valgus) by the same method—involving heel actuation—used for the other inventive foot correction devices.

What I claim is:

1. A shoe orthosis device for corrective treatment of foot deformities wherein the pressure of the posterior part of the foot on the device is transmitted to the part of the foot which is to be treated in an intermittently acting force, comprising a sole member, means within said sole member which are adapted to be operated by said pressure to rotate the forefoot around the longitudinal axis of the foot and/or move it substantially transversely to said longitudinal axis substantially about an axis perpendicular to the sole, whereby said means act on the inner side of the forefoot to lower it, thus rotating said forefoot.

2. A device as claimed in claim 1 wherein said means comprises an actuator disposed in the heel portion of said sole which is operated by said pressure and a force transmission means operatively associated with said actuator to transmit the force produced by said actuator to said forefoot.

3. A device as claimed in claim 2 adapted to produce correction of "bent foot" (talipes valgus) and "flatfoot" (fallen arches and pes supinatus, concurrent with talipes valgus), wherein said means produces a lowering of the outer side of the heel in a rotational direction opposite to that of the forefoot and further comprising particularly at least one foot support stepping plate for support of the foot connected to said sole to allow upward and downward movement thereof with respect to said sole and said actuator includes means on said stepping plate adapted to engage with and operate said force transmission means.

4. A device as claimed in claim 3 wherein said force transmission means comprises at least one strap member.

5. A device as claimed in claim 4 wherein said stepping plate is connected to said sole by hinge means, and said actuator comprises at least one roller mounted on said sole and at least one roller mounted on the bottom of said stepping surface in longitudinal closely spaced relationship, said strap passing between and over the surface of said rollers and being fastened at one end to the heel portion of said sole so that downward movement of said stepping plate will progressively increase tension on said strap.

6. A device as claimed in claim 5 wherein said rollers are disposed on the outer posterior heel portion of said sole and stepping plate, said stepping plate being pivotally connected to the sole at the outer side and said strap is connected at its forward end to the forward part of said sole and passes underneath said stepping plate in the region of the metatarsus, and a space is provided under said stepping plate in the metatarsus region to permit it to swing downwardly around said pivot, said strap exerting a downward force on said forefoot when tension force is produced by said actuator.

7. A device as claimed in claim 6 and further comprising an adjustable means on said strap to adjust the effective length of the strap and the positions of attachment of said strap are adjustable.

8. A device as claimed in claim 2 or 3 wherein said actuator comprises a chamber made of a flexible material and containing a liquid provided under the posterior part of said stepping plate, said strap extending around said chamber so that a downward motion of the stepping plate causes an expansion of the perimeter of said chamber, thus producing a tensioning force in the strap.

9. A device as claimed in any one of claims 1 to 7 for correcting pes adductus ("sickle foot") and concurrent pes supinatus, wherein the device lowers the inner side part of the forefoot (metatarsal region) and at the same time pushes it laterally.

10. A device as claimed in any one of claims 2 or 3, wherein said force transmission means comprises a rod member which produces said rotation and transverse motion.

11. A device as claimed in claim 2 or 3 wherein said force transmission means comprises a two-armed lever having a short and a long arm pivotally mounted to said sole so as to swing around an axis which is vertical to the sole, and said actuator comprises a projection on the bottom of said stepping plate, an actuating surface on said projection which runs at an angle to its direction of motion, said short arm is transverse to said longitudinal axis and is disposed in the path of travel of said actuating surface to engage with and be moved thereby about said pivot, said long arm extending in the longitudinal direction and being swung by said short arm in the transverse direction so as to rotate and move the forefoot (metatarsal region), and further comprising a loop surrounding the forefoot and extending through the transverse hollow opening in said sole, the anterior end of said long lever arm engaging said loop so that its transversely directed force acts on said loop, and the anterior inner side load surface of the sole is lower than the anterior outer side load surface of the sole.

12. A device as claimed in claim 11 wherein said long lever arm has a joint which enables the deflection of the sole or stepping plate.

13. A device as claimed in any one of claims 3 to 7 and further comprising a sliding member which acts as a rotational and transversely movable means for the forefoot slidably mounted in the sole in the region beneath said stepping plate and being operatively connected to said force transmission means and to the forefoot.

14. A device as claimed in claim 13 wherein said sliding member is disposed approximately in the plane of said stepping plate and is movable to a different angular position with respect thereto in which position said sliding member is lower on its inner side than on its outer side, pivot means for said slide mounting substantially at the outer side edge of said sole and a space underneath said sliding member into which said member and its mounting may be swung.

15. A device as claimed in claim 14 wherein an extension is provided on one of the ends of said sliding member which extends substantially vertically upwardly and a loop is provided surrounding at least part of the forefoot, one end of said loop being attached to the upper end of said extension.

16. A device as claimed in any one of claim 13 to 15 wherein said strap is fastened at its forward end to the underside of said sliding member, and further comprising a guiding roller for said strap mounted on said sole underneath said sliding member, such that when said strap is tensioned by said actuator said sliding member is lowered at the inner side or is slid transversely, or is both lowered and slid transversely.

17. A device as claimed in claim 16 wherein said sliding member is provided near the inner side with an extension which engages the great toe and furher comprising a mechanism mounted on said sole and operatively connected to said strap to move said sliding member so that it moves the great toe in the inner direction via said actuator when the heel is lowered.

18. A device as claimed in claim 17 and further comprising a pulling-cord means operatively connected to said device for producing a downward pressure on toes two through five when the heel is lowered to correct "hammer-toe" and acts together with the motion of the sliding member to correct hallux valgus of the great toe.

19. A device as claimed in claim 18 wherein a pressure plate is disposed above toes two through five, and said strap is connected to said pressure plate whereby when said strap is tensioned said toes are pressed downwardly.

* * * * *